United States Patent [19]

Yung

[11] Patent Number: 4,607,652

[45] Date of Patent: Aug. 26, 1986

[54] CONTACT LENS CLEANING APPARATUS

[76] Inventor: Simon K. C. Yung, 5, Purves Road, Jardines Lookout, Hong Kong

[21] Appl. No.: 676,004

[22] Filed: Nov. 29, 1984

[30] Foreign Application Priority Data

Aug. 29, 1984 [GB] United Kingdom ................ 8421836

[51] Int. Cl.$^4$ .............................................. B08B 3/12
[52] U.S. Cl. ................................... 134/184; 310/316; 366/127
[58] Field of Search .................... 134/1, 184; 366/127; 310/316

[56] References Cited

U.S. PATENT DOCUMENTS

| | | | |
|---|---|---|---|
| 2,814,575 | 11/1957 | Lange et al. | 134/1 |
| 2,970,073 | 1/1961 | Prange | 134/1 |
| 2,994,330 | 8/1961 | Catlin et al. | 134/58 |
| 3,007,478 | 11/1961 | Leonhardt et al. | 134/57 |
| 3,033,710 | 5/1962 | Hightower et al. | 134/1 |
| 3,034,520 | 5/1962 | Jewell | 134/99 |
| 3,278,770 | 10/1966 | Shoh | 310/316 |
| 3,291,640 | 5/1963 | Livingston | 134/1 |
| 3,371,233 | 2/1968 | Cook | 134/184 X |
| 3,402,075 | 9/1968 | Goldwasser et al. | 134/1 |
| 3,403,245 | 9/1968 | Eaton | 219/494 |
| 3,481,687 | 12/1969 | Fishman | 21/54 |
| 3,516,861 | 6/1970 | Menkes et al. | 134/1 |
| 3,640,295 | 2/1972 | Peterson | 134/159 |
| 3,672,823 | 6/1972 | Boucher | 21/54 |
| 3,697,222 | 10/1972 | Sierra | 21/54 A |
| 3,708,263 | 2/1973 | Boucher | 21/54 A |
| 3,720,402 | 3/1973 | Cummins et al. | 134/184 X |
| 3,742,492 | 6/1973 | Proctor | 310/316 X |
| 3,771,772 | 11/1973 | Honda | 366/127 X |
| 3,866,068 | 2/1975 | Krenicki et al. | 310/316 |
| 3,871,395 | 3/1975 | Murry | 134/184 X |
| 3,912,450 | 10/1975 | Boucher | 21/54 A |
| 3,990,906 | 11/1976 | Johnston et al. | 134/1 |
| 4,211,744 | 7/1980 | Boucher | 422/20 |
| 4,271,371 | 6/1981 | Furuichi et al. | 310/316 |
| 4,382,824 | 5/1983 | Halleck | 134/1 |

FOREIGN PATENT DOCUMENTS 947699 1/1964 United Kingdom .

OTHER PUBLICATIONS

Bulat, T. V. "The Present State-of-the-Art in Sonic Cleaning," Journal of the American Association for Contamination Control, Oct., 1965.

*Primary Examiner*—Philip R. Coe
*Attorney, Agent, or Firm*—Lyon & Lyon

[57] ABSTRACT

Contact lens cleansing apparatus comprises at least one cavity for containing a contact lens together with cleansing a liquid. An ultrasonic transducer applies ultrasonic frequency mechanical vibrations to the liquid and lens contained in the cavity. Oscillating means for driving ultrasonic transducer at a substantially stable resonant frequency includes a dual ferrite core transformer feedback circuit which minimizes energy consumption. There is also a timer whose operation is controlled from the oscillating means. Simultaneous cleaning and sterilizing of a contact lens is achieved.

10 Claims, 4 Drawing Figures

CONTACT LENS CLEANING APPARATUS

BACKGROUND OF THE INVENTION

This invention relates to the cleaning and/or sterilizing or disinfecting of contact lenses. In particular the invention relates to apparatus in which the cleaning and/or sterilizing or disinfecting of the lenses is effected by immersing the lenses in a sterilizing or saline solution or antiseptic fluid and subjecting the lenses to ultrasonic vibrations. By the term "cleansing" the applicant includes the terms "cleaning and/or sterilizing or disinfecting".

To avoid eye infections it is highly desirable that contact lenses be thoroughly cleaned and sterilized or disinfected at regular intervals. Some systems have proposed immersing the lenses in a cleaning or sterilizing liquid and also heating the liquid. Such systems have not proved very satisfactory in practice.

It has also been proposed to use ultrasonic vibrations to assist but the apparatus used has generally been rather bulky and complicated. It is therefore an object of the invention to provide a relatively simple and readily portable apparatus for conducting this type of cleaning and/or sterilization or disinfecting of contact lenses.

SUMMARY OF THE INVENTION

Contact lens cleansing apparatus comprises at least one cavity for containing at least one contact lens and cleansing liquid, and an ultrasonic transducer for applying ultrasonic frequency mechanical vibrations to the liquid and lens contained in the cavity. Oscillating means is included for driving the ultrasonic transducer includes a ferrite core transformer feedback circuit to stabilize the resonant frequency of the ultrasonic transducer means.

Also included is a timer whose operation is controlled from the oscillating means for energizing the oscillator means for a predetermined period of time.

Such apparatus operates relatively efficiently and so can use as its power supply a simple DC battery supply. It does not therefore require to use a mains supply. The efficiency of the operation is promoted by the use of a dual ferrite core transformer feedback circuit. The apparatus can therefore be quite compact and can be readily portable.

Also the use of the dual ferrite core transformer feedback circuit ensures a relatively steady resonant frequency for the ultrasonic transducer irrespective of the variations in the amount of and/or the size and type of lens in the cavity. Further variations in the type of sterilizing liquid, the supply voltage and the temperature also largely unaffect the resonant frequency. At resonance the transducer is most effective in sterilization, and the frequency is in the range of 20 to 40 KHz. Because of this, the resonant frequency is sufficiently constant for that frequency to be used to control the operation of an associated timer which can be used to predetermine the period of operation. Thus it is important that the lenses be given sufficient length of cleaning but that they be not subjected to excessive periods of ultrasonic vibration which could otherwise damage or impair the quality of the lenses. It has been proven scientifically that ultrasonic vibrations will not damage contact lens.

Further the apparatus is effective in sterilizing lenses because the frequency of the vibrations in the cavity is resonant and largely constant which has been found to promote the killing and removal of bacteria and virus.

The apparatus of the invention can use a saline solution or sterilizing solution which will then have the effect of both sterilizing and, in the presence of the ultrasonic vibrations, cleaning the lenses. This is in contrast with some prior types of apparatus which have used heat to sterilize the lens or have merely used chemicals to sterilize the lens without the cleaning effect of the ultrasonic vibrations.

The conventional means of sterilization of contact lenses usually requires specialized disinfecting or sterilizing solutions which are more expensive than the saline solution on a unit volume basis. Since the contact lens cleansing apparatus substantially destroys bacteria and virus with saline solution only, the contact lens user will spend less on sterilizing saline solution with the said contact lens cleansing apparatus. Preferably all bacteria and virus in the human eye is destroyed by said vibration in said saline solution.

An example of apparatus for cleansing contact lenses is described with reference to the accompanying drawings.

DETAILED DESCRIPTION

Figure 1:
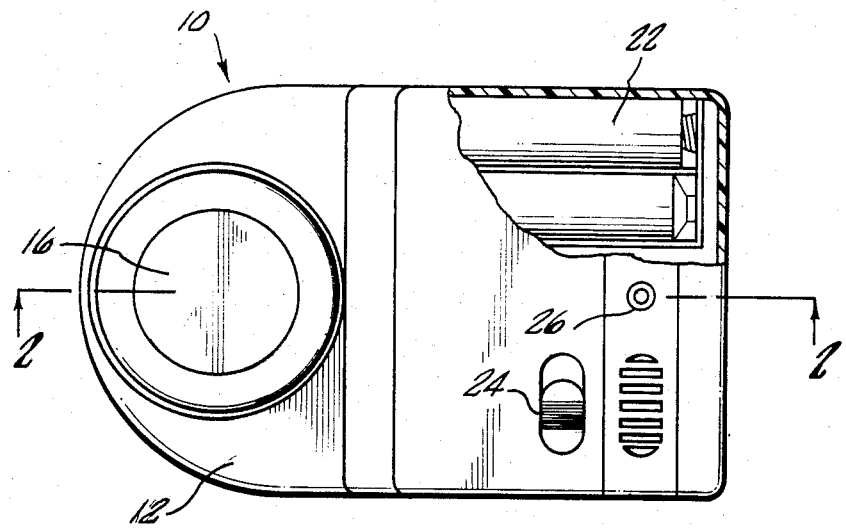
FIG. 1 is a broken-away plan view of the apparatus.
Figure 2:
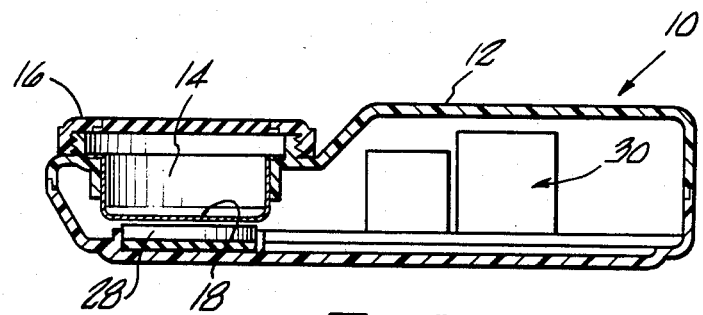
FIG. 2 is a section taken along the line 2—2 of FIG. 1.

The apparatus 10 comprises a housing 12 in which is formed a cavity 14. This cavity 14 is of bowl shape as is best shown in FIG. 2 and is intended to hold contact lenses for cleaning and/or sterilizing. It is covered by a removable screw-on cap 16. The cavity has a flat base 18 and to the underside of this is adhered an ultra-sonic transducer 20.

The housing 12 is of compact portable size such that it could conveniently be carried in a pocket. The apparatus has its own power supply 22 in the form of dry batteries contained within the housing. Also a manually operated switch 24 for controlling operation is provided together with an indicator light 26 to show when the apparatus is working.

Figure 3:
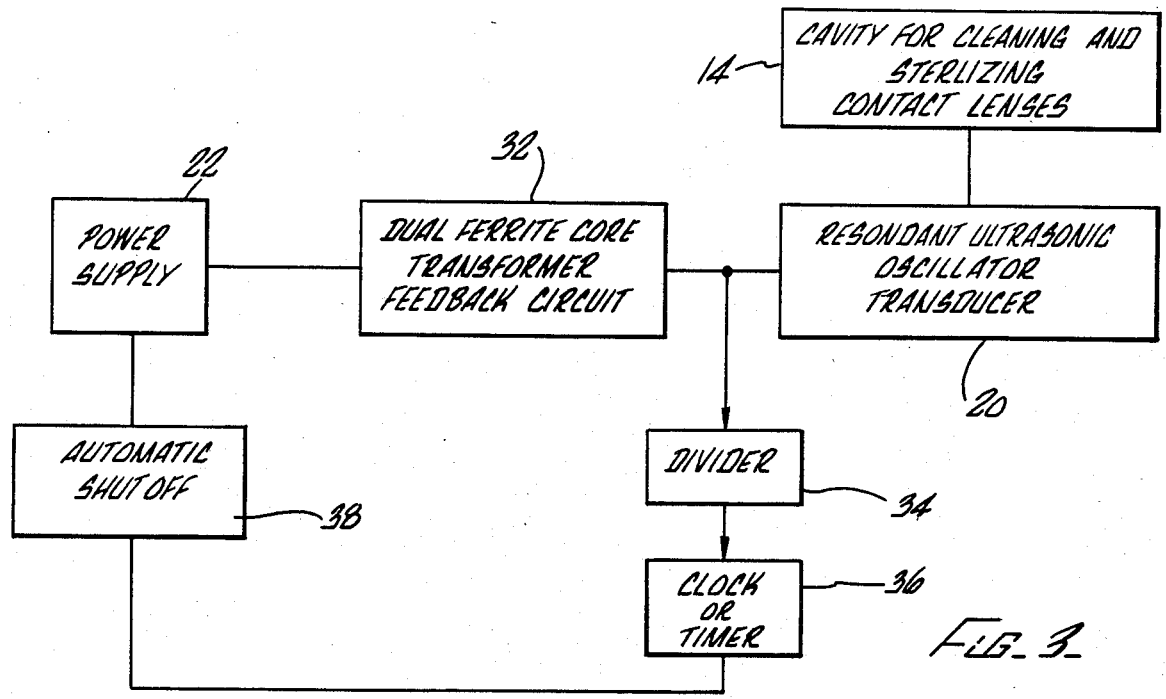
FIG. 3 is a block diagram illustrating the operation of the apparatus.
Figure 4:
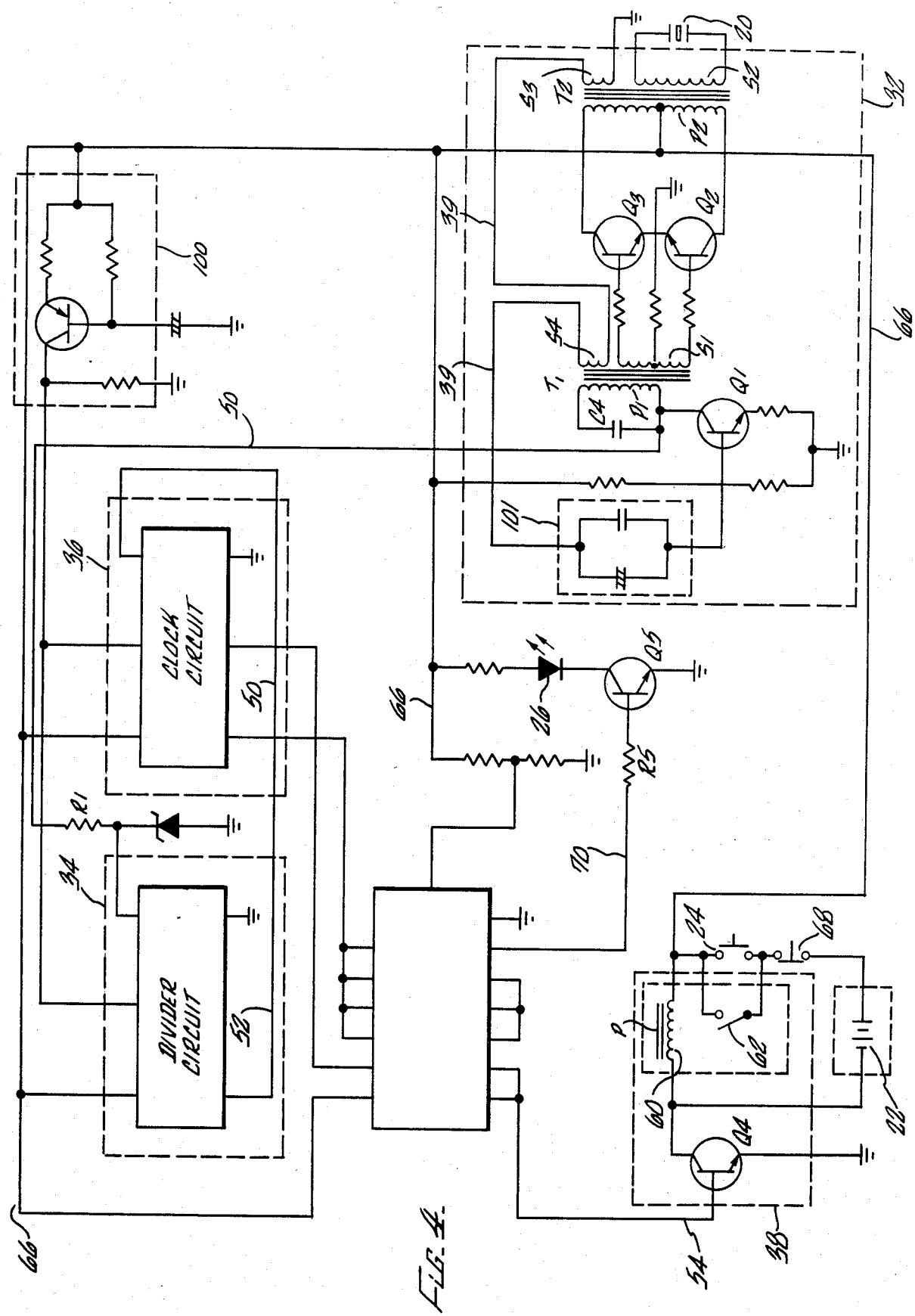
FIG. 4 is a circuit diagram of the electronic components in the apparatus.

In the housing, electronic circuitry 30 for operating the transducer is provided and that circuitry 30 is shown diagrammatically in FIG. 3 and in more detail in FIG. 4. The circuitry 30 includes a dual ferrite core transformer feedback oscillator circuit 32 whose output drives the transducer 20. An output is taken from the circuit 32 to a counter and divider circuit 34 and in turn to a clock circuit 36. Thus the timing of the circuit 36 is thus controlled by the oscillating frequency from the oscillator circuit. The timer in turn controls the operation of the circuit 32 by means of a shut-off switch 38 which controls the power supply 22.

Thus, the user places the contact lenses and sterilizing or disinfecting solution in the cavity 14 and closes it with the cap 16. The user then activates the circuit 32, and the ultrasonic vibrations supplied by the transducer 20 to the cavity clean the lens or lenses. The circuits 34 and 36 reach a preset time and then the shut-off switch 38 disconnects the power supply 22 to the circuit 32 to terminate the cleaning and sterilizing and thereafter the user removes the cleaned lenses from the cavity 14.

FIG. 4 shows the oscillator circuit 32 including two ferrite cored transformers T1 and T2. An oscillating loop is formed by a capacitor C4 and the primary coil P1 of the transformer T1 and this is driven by transistor Q1. The output of the secondary coil S1 of the transformer is used in a push-pull amplifying circuit comprising the transistors Q2 and Q3 to drive the primary coil P2 of the transformer T2. The secondary coil S2 of the transformer T2 in turn drives the transducer 20.

Feedback is supplied by secondary coils S3 and S4 of the transformers T1 and T2, respectively, along line 39 to the transistor Q1 to ensure that the whole circuit 32 oscillates resonantly and the coils S3 and S4 couple the two transformers together. Also the resonant frequency is kept largely constant by this known arrangement irrespective of changes in the transducer 20. Thus the transducer will be affected by the physical characteristic of the lens and liquid such as the amount of liquid placed in the cavity 14 and the size and type of contact lens and further by factors such as temperature and type of liquid. Despite this, the feedback in the circuit 32 ensures that the whole circuit remains in resonance and despite these changes the resonant frequency will only be insignificantly affected, e.g. by less than 500 Hz. The resonant frequency should be in the range of 20 to 40 KHz depending on the quality and grade of a circuitry material.

The circuit is also very efficient in its use of power and so an effective ultrasonic output at the resonant frequency to the cavity 14 can be provided by a power source 22 composed of dry batteries.

Because the oscillating frequency of the circuit 32 is substantially constant, it can be used to control the period of operation of the apparatus 10. Thus an output is taken along the line 50 from the oscillating loop formed by the capacitor C4 and the primary coil P1 of transformer T1 and that output is fed via resistor R1 to an integrated circuit IC1. A zener diode 21 limits the pulse height of the output. The latter integrated circuit IC1 acts as a divider and thus reduces the frequency of the oscillating pulses to a countable rate.

The resulting output from this circuit IC1 passes along line 52 to integrated counter circuit IC2 which acts as a clock. When the circuit 30 is initially activated the clock counter in circuit IC2 is set to zero and then counts up to a preset number. Since the oscillating output taken along the line 50 is substantially constant, the circuit IC2 acts therefore as a timer and when its count reaches that preselected number an output along line 53 is supplied to a further chip IC3. The latter chip IC3 provides an output along line 54 which, when the overall circuit is activated, is applied to the base of a transistor Q4 which then conducts freely. As a result the relay coil 60 of a relay RY in series is activated. This has the effect of holding the switch contacts 62 of the relay RY closed so as to keep the overall circuit 30 activated from the power supply 22 via the positive line 66. When the clock circuit IC2 reaches its predetermined count, however, the output to chip IC3 causes the latter to disable the transistor Q4 and as a result the switch contacts 62 open and the overall circuit 30 is disabled.

In parallel with the switch contacts 62 is provided the manually operated switch 24. As can be seen this has a relaxed off position. Thus when the user wishes to activate the apparatus he closes that switch temporarily to by-pass the switch contacts 62 and activate the overall circuit by the lines 66. The oscillating circuit 32 begins and the clock circuit IC2 is reset so that in turn the transistor Q4 becomes highly conducive. The switch contacts 62 of the relay RY therefore close and so when the user releases the swtich 24 actuation of the circuit continues while the clock circuit IC2 continues to count.

A cutout safety switch 68 is provided in series with the switch 24 and acts as a safety measure.

A further output is taken from the circuit IC3 along a line 70 and through resistor R5 to a transistor Q5 in series with a light emitting diode constituting the indicator light 26. This output along line 70 enables the transistor Q5 to conduct in the same way as and simultaneously with the transistor Q4 and so all the time that the circuit is operating the transistor Q5 remains conductive and the light emitting diode 26 remains illuminated. When the circuit IC2 reaches its predetermined count, however, the output from the chip IC3 along line 70 disables the transistor Q5 and so extinguishes the indicator light 26.

The transistor circuit 100 serves as a reset circuit by applying suitable pulses to the divider circuit IC1 and clock circuit IC2. Circuits elements 101 connected in the feedback line 39 transmits the feedback frequency and also acts to isolate the DC as necessary.

Many changes and variations may be made providing different embodiments without departing from the scope of this invention. The matter contained in the above description is illustrative and not limiting, the invention being interpreted solely by the scope of the appended claims.

I claim:

1. Contact lens cleansing apparatus comprising at least one cavity for containing at least one contact lens and cleansing liquid, an ultrasonic transducer for applying ultrasonic frequency mechanical vibrations to the liquid and contact lens contained in said cavity, DC powered oscillating means for driving the ultrasonic transducer at a substantially stable resonant frequency in the range 20 to 40 kHz, said oscillating means including a dual ferrite core transformer feedback circuit, and a timer for energization of the oscillatiing means for a predetermined period of time, said timer being controlled by the resonant frequency of the oscillating means.

2. Contact lens cleansing apparatus as claimed in claim 1 wherein the power is obtained from a DC battery supply.

3. Contact lens cleansing apparatus comprising at least one cavity for containing at least one contact lens together with cleansing liquid, an ultrasonic transducer for applying ultrasonic frequency mechanical vibrations to the liquid and lens contained in the cavity, oscillating means for driving the ultrasonic transducer, said oscillating means including a dual ferrite core transformer feedback circuit for providing a substantially stable resonant frequency to the ultrasonic transducer means substantially independently of the nature of the lens and cleansing liquid physical characteristic.

4. Contact lens cleansing apparatus as claimed in claim 3 including a timer for energizing the oscillating means for a predetermined period of time, said timer operation being controlled by the oscillating means.

5. Apparatus for simultaneously cleaning and sterilizing a contact lens comprising at least one cavity for containing said contact lens together with a contact lens cleansing liquid or saline solution, an ultrasonic transducer for applying ultrasonic frequency mechanical vibrations to the liquid and the lens contained in the cavity thereby to clean the lens, oscillating means for driving the ultrasonic transducer at a substantially stable resonant frequency, such oscillating means including a dual ferrite core transformer feedback circuit to provide such stabilized resonant frequency, and a timer for energizing the oscillating means for a predetermined period of time for simultaneous cleaning and sterilization of the lens.

6. Contact lens cleansing apparatus comprising at least one cavity for containing at least one contact lens together with saline solution, an ultrasonic transducer for applying ultrasonic frequency mechanical vibrations to the liquid and the lens contained in the cavity thereby to clean the lens, oscillating means including a dual ferrite core transformer feedback circuit for providing a substantially stable resonant frequency to the ultrasonic transducer, whereby bacteria and virus may be substantially destroyed by said vibrations in said saline solution.

7. Contact lens cleansing apparatus as claimed in either claim 1 or 3 wherein the cleansing liquid is a saline solution.

8. Contact lens cleansing apparatus as claimed in claim 6 wherein all bacteria and virus in the human eye is destroyed by said vibration in said saline solution.

9. Apparatus as claimed in any of claims 1, 3, 5 or 6 wherein the feedback circuit includes a push-pull oscillator.

10. Apparatus as claimed in any of claims 1, 3, 5 or 6 wherein the resonant frequency is maintainable within a band of 1 kHz centered on a preselected resonant frequency.

* * * * *